United States Patent
Xu et al.

(10) Patent No.: US 11,547,593 B2
(45) Date of Patent: Jan. 10, 2023

(54) PEDIATRIC SUPPORT MODULE FOR PATIENT SUPPORT APPARATUS

(71) Applicant: Stryker Corporation, Kalamazoo, MI (US)

(72) Inventors: Shaofei Wilson Xu, Kalamazoo, MI (US); Brandon David Naber, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 902 days.

(21) Appl. No.: 16/271,124

(22) Filed: Feb. 8, 2019

(65) Prior Publication Data

US 2019/0247219 A1 Aug. 15, 2019

Related U.S. Application Data

(60) Provisional application No. 62/629,240, filed on Feb. 12, 2018.

(51) Int. Cl.
*A61F 5/37* (2006.01)
*A61G 1/02* (2006.01)
(Continued)

(52) U.S. Cl.
CPC .......... *A61F 5/3784* (2013.01); *A61G 1/0237* (2013.01); *A61G 1/04* (2013.01); *A61G 1/044* (2013.01); *A61G 5/10* (2013.01); *A61G 7/0526* (2013.01); *B60N 2/00* (2013.01); *A61B 2050/314* (2016.02); *A61G 1/0218* (2013.01);
(Continued)

(58) Field of Classification Search
CPC . A61F 5/37; A61F 5/3769–3784; A61G 5/10; A61G 1/013; A61G 1/02–0268; A61G 1/04; A61G 1/044; A61G 2200/14; A61G 1/00–06; A61G 7/00–05; A61G 7/0504–0528; B60N 2/00; B60N 2/005; A61B 50/30; A61B 50/31; A61B 2050/314
See application file for complete search history.

(56) References Cited

U.S. PATENT DOCUMENTS 2,777,138 A * 1/1957 Gallagher ............ A47D 15/006
5/655
3,770,919 A 11/1973 Lewis
(Continued)

OTHER PUBLICATIONS

Ferno, "Patient Restraint Systems Webpage", http://www.ferno.com.au/products/emergency-and-rescue/patient-handling/patient-restraint-systems, 2019, 6 pages.
(Continued)

*Primary Examiner* — Michelle J Lee
(74) *Attorney, Agent, or Firm* — Howard & Howard Attorneys PLC

(57) ABSTRACT

A patient support apparatus comprises a support structure comprising a head end, a foot end, a base, and a patient support deck. The patient support deck comprises a fowler section at the head end and a foot section at the foot end. The fowler section is capable of articulating relative to the base. The patient support apparatus further comprises a pediatric support module comprising a seat section disposed between the fowler section and the foot section. The pediatric support module is integrated into the patient support deck and comprises a lid and a body.

10 Claims, 13 Drawing Sheets

(51) Int. Cl.
  *A61G 1/04*   (2006.01)
  *A61G 1/044*  (2006.01)
  *A61G 5/10*   (2006.01)
  *A61G 7/05*   (2006.01)
  *B60N 2/00*   (2006.01)
  *A61B 50/30*  (2016.01)
  *A61B 50/00*  (2016.01)

(52) U.S. Cl.
  CPC ........ *A61G 1/0268* (2013.01); *A61G 2200/14* (2013.01)

(56) References Cited

U.S. PATENT DOCUMENTS

| | | | |
|---|---|---|---|
| 3,781,497 A | | 12/1973 | Stephenson et al. |
| 3,996,648 A | | 12/1976 | Romanzi, Jr. |
| 4,926,528 A | | 5/1990 | Matsuki |
| 4,977,630 A | * | 12/1990 | Oswalt ............... A61G 1/00 297/440.22 |
| 5,400,448 A | * | 3/1995 | Zwickey ............. A61H 31/008 5/628 |
| 5,537,700 A | | 7/1996 | Way et al. |
| 5,860,176 A | * | 1/1999 | Norberg .............. A61G 1/00 5/628 |
| 6,694,578 B1 | | 2/2004 | Nicoll |
| 6,966,087 B2 | * | 11/2005 | Robinette ............ A61F 5/3784 5/628 |
| 7,398,571 B2 | | 7/2008 | Souke et al. |
| 8,763,177 B2 | * | 7/2014 | Shah ................. A61G 13/123 5/655 |
| 10,080,693 B1 | | 9/2018 | Scheenstra et al. |
| 2004/0045089 A1 | * | 3/2004 | Zucker .............. A61G 1/04 5/628 |
| 2012/0186588 A1 | * | 7/2012 | Wilson .............. A61N 5/1049 128/845 |
| 2016/0302985 A1 | | 10/2016 | Tessmer et al. |
| 2017/0246065 A1 | | 8/2017 | Connell et al. |

OTHER PUBLICATIONS

Quadmed, Inc., "The Q Blog—Featuring the ACR4 Ambulance Child Restraint from Quantum EMS!", 2012, http://emsproducts.blogspot.com/2016/09/featuring-acr4-ambulance-child.html?_sm_au_=iVV6q1jk51VM0W0r, 2 pages.

Stryker, "Power-PRO XT, Ref. 6506 Operations/Maintenance Manual—Attaching the Pedi-Mate Infant Restraint System", 6506-109-001, Rev E, Jun. 2015, p. 66.

Advanced Healthcare Technology, "The Baby Pod Range from Advanced Healthcare Technology Webpage", http://www.babypod.com/, 2019, 3, pages.

Dorel Juvenile, "Maxi Cosi Car Seats Webpage", https://www.maxicosi.com/us-en/car-seats/, 2016-2019, 10 pages.

Ferno, "Pedi-Mate Webpage", http://www.fernoems.com/en/search-results/pedi-mate.aspx, 2019, 1 page.

Life-Assist, Inc., "Life-Assist Emergency Medical Products Webpage", https://legacy.life-assist.com/, 2003-2019, 1 page.

Schnitzler Rettungspordukte Gmbh und Co. KG, "Pediatric Restraint System Integraged in Stretcher-Support for All Stretcher Types Flyer", http://www.schnitzler-transportgeraete.de/mediapool/139/1393780/data/Flyer_BabyKinderR_ckhaltesysteme_integrated_englisch_09-2015.pdf, Sep. 2015, 1 page.

Schnitzler Rettungspordukte Gmbh und Co. KG, "Pediatric Restraint System Removable in Stretcher-Support for All Stretcher Types Flyer", http://www.schnitzler-transportgeraete.de/mediapool/139/1393780/data/Flyer_BabyKinderR_ckhaltesysteme_removable_englisch_09-2015.pdf, Sep. 2015, 1 page.

* cited by examiner

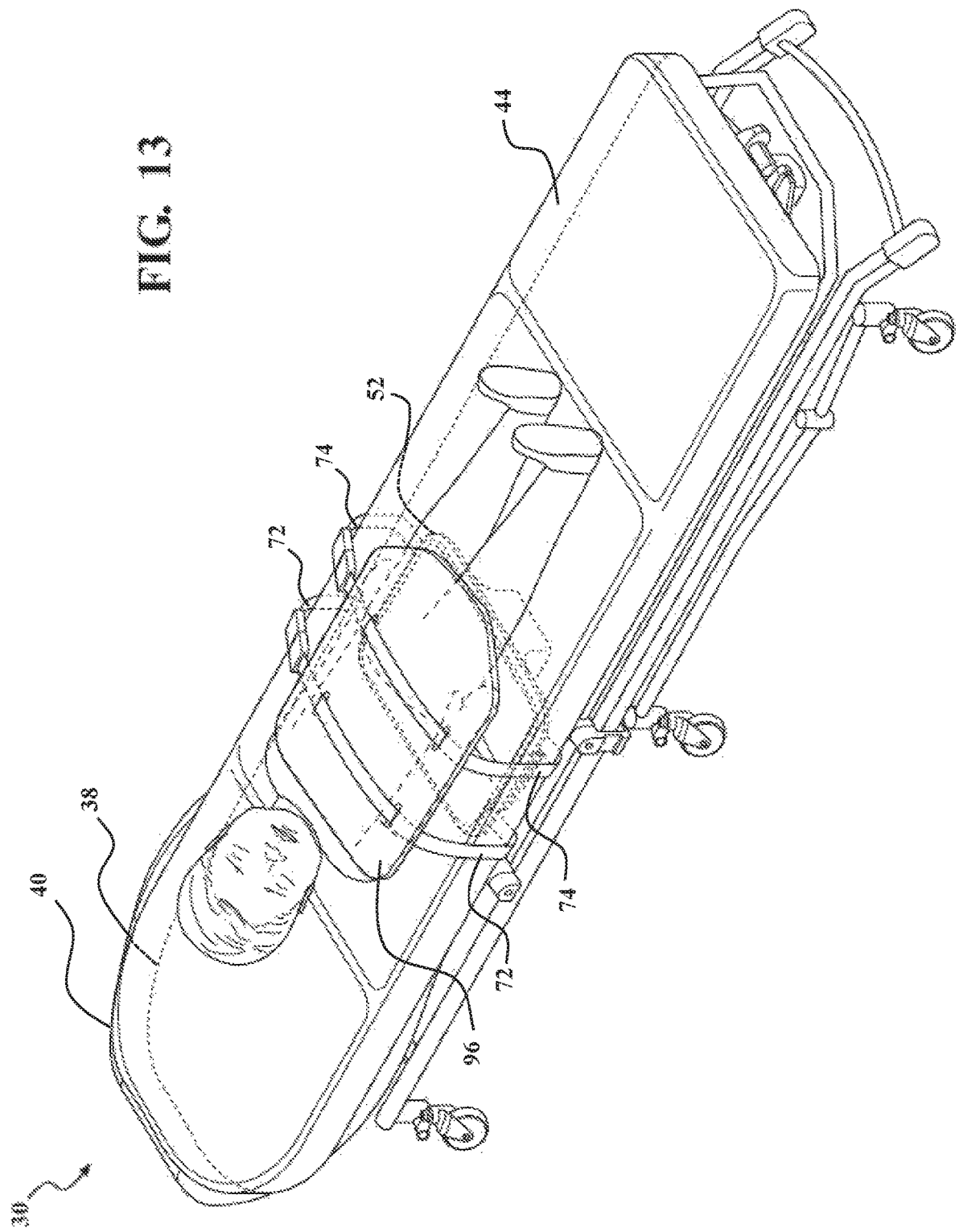

PEDIATRIC SUPPORT MODULE FOR PATIENT SUPPORT APPARATUS

CROSS-REFERENCE TO RELATED APPLICATION

The subject patent application claims priority to and all the benefits of U.S. Provisional Patent Application No. 62/629,240 filed on Feb. 12, 2018, the disclosure of which is hereby incorporated by reference in its entirety.

BACKGROUND

Patient support apparatuses, such as cots, hospital beds, stretchers, tables, wheelchairs, and chairs facilitate care of patients in a health care setting. Conventional patient support apparatuses comprise a support structure having a base, a frame, and a patient support deck on the frame upon which the patient is supported. However, most conventional patient support apparatuses are designed for adult patients and are ill equipped to support and/or restrain pediatric patients. Therefore, standalone products made for supporting and restraining pediatric patients often must be used. Because these products are not integrated into the patient support apparatus, they are not always available when they are needed (e.g., emergency personnel must remember to bring the product with them on emergency calls; in a healthcare setting, the product must be retrieved if not in the immediate vicinity when needed; etc.). Moreover, such standalone products can be difficult, confusing, or time-consuming to attach to the patient support apparatus, which can expend valuable time as well as the attention of healthcare personnel, both of which are particularly vital during a medical emergency.

A pediatric support module for a patient support apparatus is desired that addresses one or more of the aforementioned challenges.

BRIEF DESCRIPTION OF THE DRAWINGS

FIG. 13 is a perspective view of the patient support apparatus in a fifth apparatus configuration with the pediatric support module in the third module configuration.

DETAILED DESCRIPTION

Figure 1:
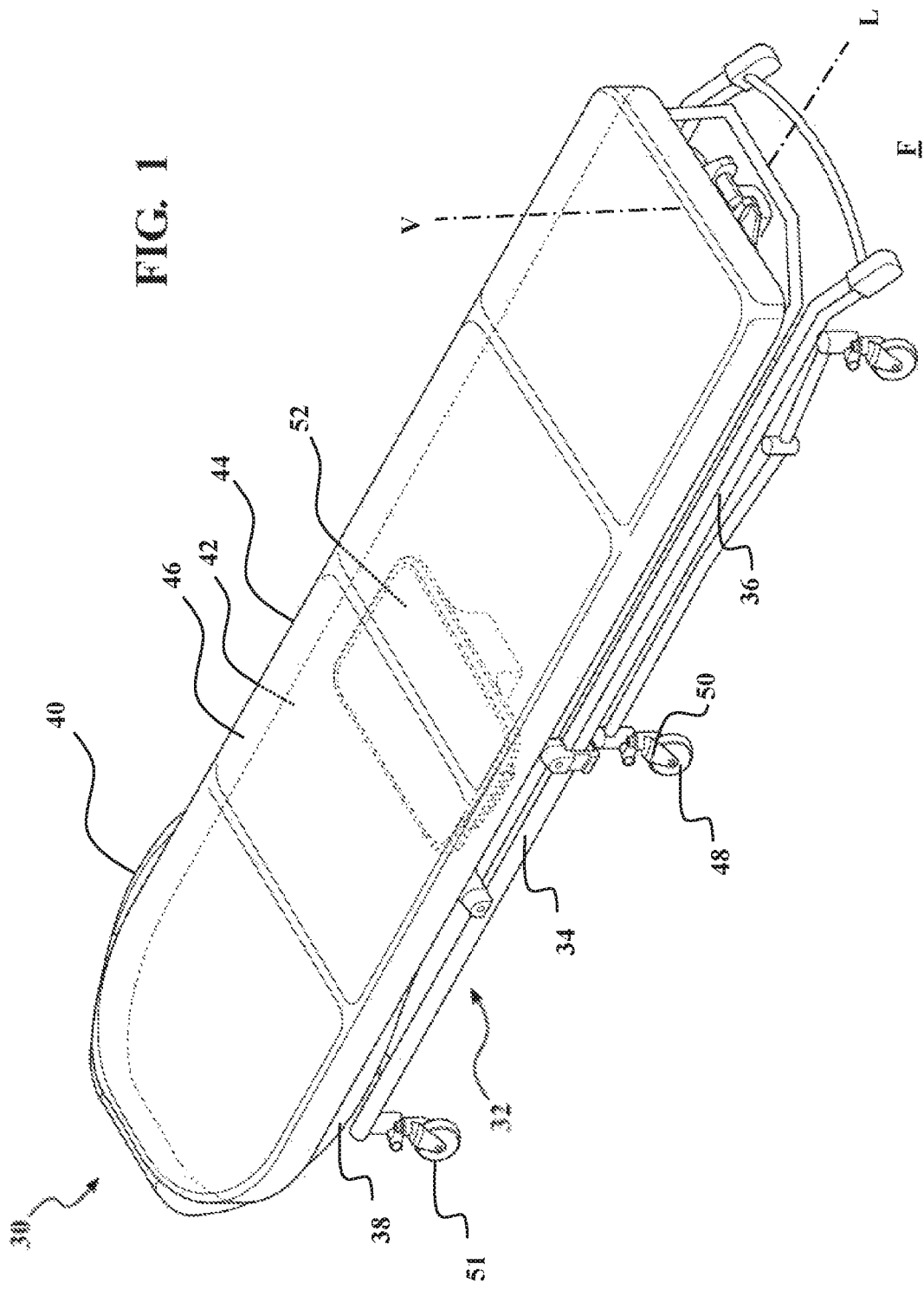
FIG. 1 is a perspective view of a patient support apparatus in a first apparatus configuration with a pediatric support module in a first module configuration.

Referring to FIG. 1, a patient support apparatus 30 is shown for supporting a patient in a health care setting. In the representative embodiment illustrated herein, the patient support apparatus 30 is realized as a mobile cot that is utilized to transport patients, such as from an emergency site to an emergency vehicle (e.g., an ambulance). However, as will be appreciated from the subsequent description below, the patient support apparatus 30 may comprise a hospital bed, stretcher, table, wheelchair, chair, or similar apparatus utilized in the care of a patient.

A support structure 32 provides support for the patient. The support structure 32 illustrated in FIG. 1 comprises a base 34 and a support frame 36. The support structure 32 also comprises a patient support deck 38 disposed on the support frame 36. The patient support deck 38 comprises sections, some of which are capable of articulating (e.g., pivoting) relative to the support frame 36, such as a fowler (back) section 40 and a leg section 41 (see FIG. 2). The patient support deck 38 provides a patient support surface 42 upon which the patient is supported.

A mattress 44 is disposed on the patient support deck 38 during use. The mattress 44 comprises a secondary patient support surface 46 upon which the patient is supported. The base 34, support frame 36, patient support deck 38, and patient support surfaces 42, 46 each have a head end and a foot end corresponding to designated placement of the patient's head and feet on the patient support apparatus 30. The base 34 comprises a longitudinal axis L along its length from the head end to the foot end. The base 34 also comprises a vertical axis V arranged crosswise (e.g., perpendicularly) to the longitudinal axis L along which the support frame 36 is lifted and lowered relative to the base 34. The construction of the support structure 32 may take on any known or conventional design, and is not limited to that specifically set forth above. In addition, the mattress 44 may be omitted in certain embodiments, such that the patient rests directly on the patient support surface 42.

Side rails (not shown) may be coupled to the support frame 36 in some embodiments. Depending on the specific configuration of the patient support apparatus 30, it will be appreciated that there could be different types and/or arrangements of various numbers of side rails. The side rails may be fixed to the support frame 36 or may be movable between a raised position in which they block ingress and egress into and out of the patient support apparatus 30, one or more intermediate positions, and a lowered position in which they are not an obstacle to such ingress and egress. In still other configurations, such as in the illustrated embodiment, the patient support apparatus 30 may not include any side rails.

Wheels 48 are coupled to the base 34 to facilitate transport over the floor surface F. In the embodiment shown, the wheels 48 are caster wheels able to rotate and swivel relative to the support structure 32 during transport. Each of the wheels 48 forms part of a caster assembly 50. Each caster assembly 50 is mounted to the base 34. It should be understood that various configurations of the caster assemblies 50 are contemplated. As shown, two of the wheels 48 comprise loading wheels (one of which is labeled 51). The loading wheels 51 extend from the base 30 proximate to the head end of the patient support surface 42 to facilitate loading and unloading of the patient support apparatus 30 from a vehicle. For example, the loading wheels 51 may be positioned and configured to facilitate loading and unloading the patient support apparatus 30 into an ambulance. In addition, in some embodiments, the wheels 48 are not caster wheels and may be non-steerable, steerable, non-powered, powered, or combinations thereof. Additional wheels are also contemplated. For example, the patient support apparatus 30 may comprise four non-powered, non-steerable wheels, along with one or more powered wheels. In some cases, the patient support apparatus 30 may not include any wheels.

In other embodiments, one or more auxiliary wheels (powered or non-powered), which are movable between stowed positions and deployed positions, may be coupled to the support structure 32. In some cases, when these auxiliary wheels are located between caster assemblies 50 and contact the floor surface F in the deployed position, they cause two of the caster assemblies 50 to be lifted off the floor surface F thereby shortening a wheel base of the patient support apparatus 30. An additional wheel may also be arranged substantially in a center of the base 34.

The patient support apparatus 30 may further comprise a lift system (not numbered) that operates to lift and lower the support frame 36/patient support deck 38 relative to the base 34. The lift system is configured to move the support frame 36/patient support deck 38 to any desired position. One exemplary lift system is described in U.S. Patent Application Pub. No. 2017/0246065, filed on Feb. 22, 2017, entitled "Lift Assembly for Patient Support Apparatus," hereby incorporated by reference herein in its entirety. Other types of lift systems can also be used, such as those described in U.S. Patent Application Publication No. 2016/0302985, filed on Apr. 20, 2016, entitled "Patient Support Lift Assembly," hereby incorporated by reference herein in its entirety, and U.S. Pat. No. 7,398,571, filed on Jun. 30, 2005, entitled, "Ambulance Cot and Hydraulic Elevating Mechanism Therefor," hereby incorporated herein by reference.

Referring to FIG. 1, the patient support apparatus 30 is shown in a first apparatus configuration, with a pediatric support module 52 shown in a first module configuration. In the first apparatus configuration, the patient support deck 38 of the patient support apparatus 30 is completely flat, covered by the mattress 44. The pediatric support module 52 is disposed below the mattress 44 and integrated into the patient support deck 38. In the first module configuration, the pediatric support module 52 is closed, and in some cases locked, and entirely contained within the patient support apparatus 30, such that it is not visible from above the mattress 44.

In some embodiments, the pediatric support module 52 may be removable from the patient support apparatus 30. This may be useful when there are two patients to transport, where one is an adult and one is a child. For instance, emergency personnel may need to transport an adult patient, but there may also be a child present. The child may be a patient or may simply be present without any other adults to look after the child when the adult patient is being transported via ambulance. Therefore, in either case, the child will need to be transported along with the adult patient. In such situations, it may be useful to be able to remove the pediatric support module 52 and use it as a standalone unit. For instance, it may be strapped into a seat (or to another surface) within the ambulance so that the child may be safely transported in the vehicle, and the patient support apparatus 30 is still fully operational and be used to transport the adult patient.

Figure 2:
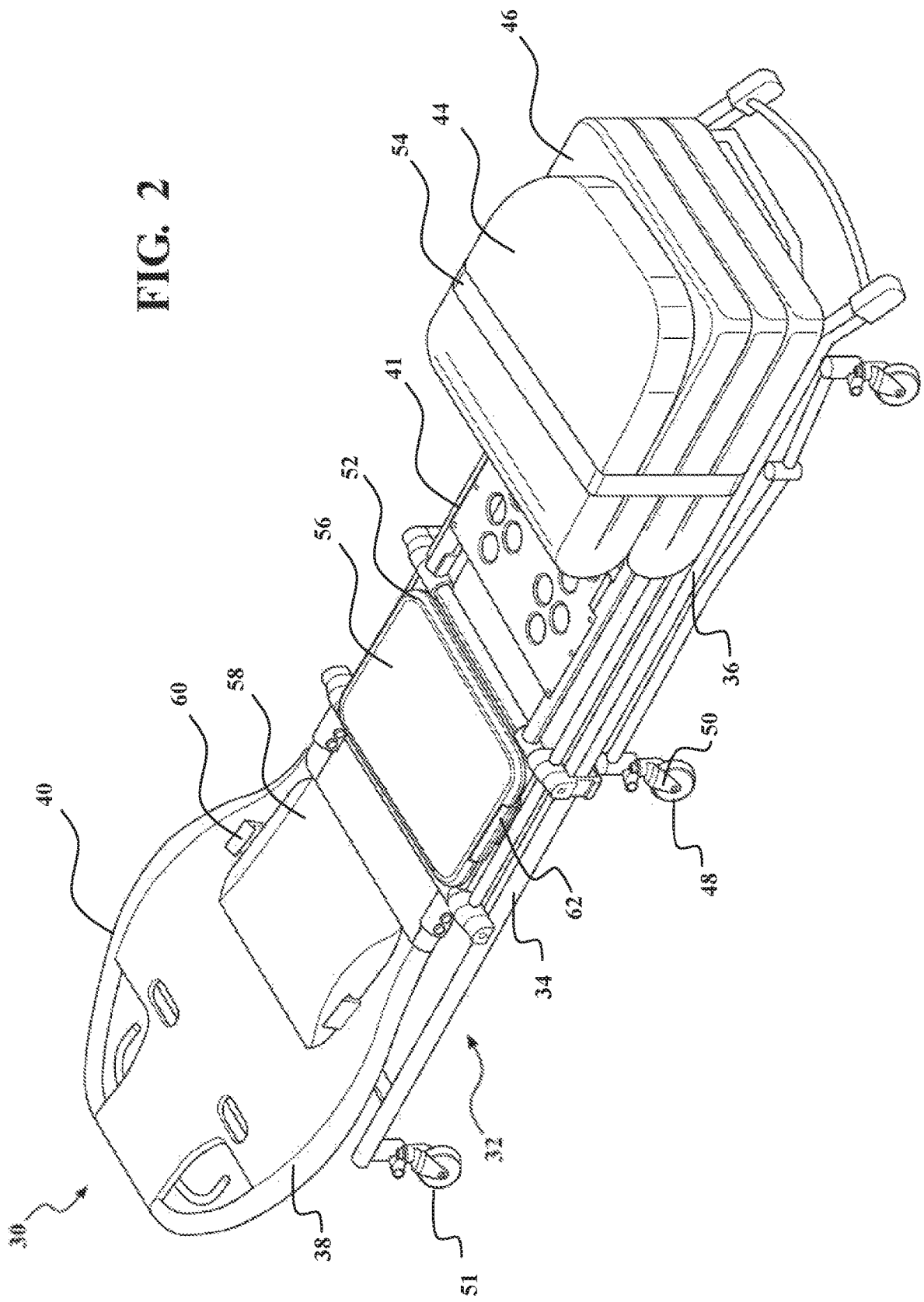
FIG. 2 is a perspective view of the patient support apparatus in a second apparatus configuration with the pediatric support module in the first module configuration.

Referring now to FIG. 2, the patient support apparatus 30 is shown in a second apparatus configuration with the pediatric support module 52 in the first module configuration. In the second apparatus configuration, the mattress 44 is folded and restrained at one end of the patient support apparatus 30 by a mattress strap 54. The patient support deck 38 is exposed, such that a module lid 56 of the pediatric support module 52 is visible. The module lid 56 is disposed at the same level as or below the fowler section 40 and, when closed, acts as a seat section of the patient support deck 38. The remainder of the pediatric support module 52 is integrated into the patient support deck 38.

According to the illustrated embodiment, an optional lid connector 58 may be integrated into the fowler section 40 of the patient support apparatus 30. The lid connector 58 may include one or more acceptor latches 60 for accepting and locking in place the module lid 56 (see FIG. 5). It will be understood that any suitable type of latch may be used. In the illustrated embodiment, acceptor latches 60 comprise flexible tabs (e.g., resilient detents) that may be flexed outwardly to accept the module lid 56 and snap back into place in a snap-fit manner when released to lock the module lid 56 in place. The acceptor latches 60 may again be flexed outwardly to eject the module lid 56. Use of the lid connector 58 may be desirable to keep the pediatric support module 52 in place, especially where the pediatric support module 52 is in an ambulance/vehicle that is moving at high rates of speed or may even be involved in a collision. Other forms of restraints for securing the module lid 56 to the fowler section 40 are also contemplated. For instance, restraints used on the patient support apparatus 30 to secure adult patients may be used to secure the module lid 56, such as by slots in the module lid 56 that accept the restraints.

Figure 3:
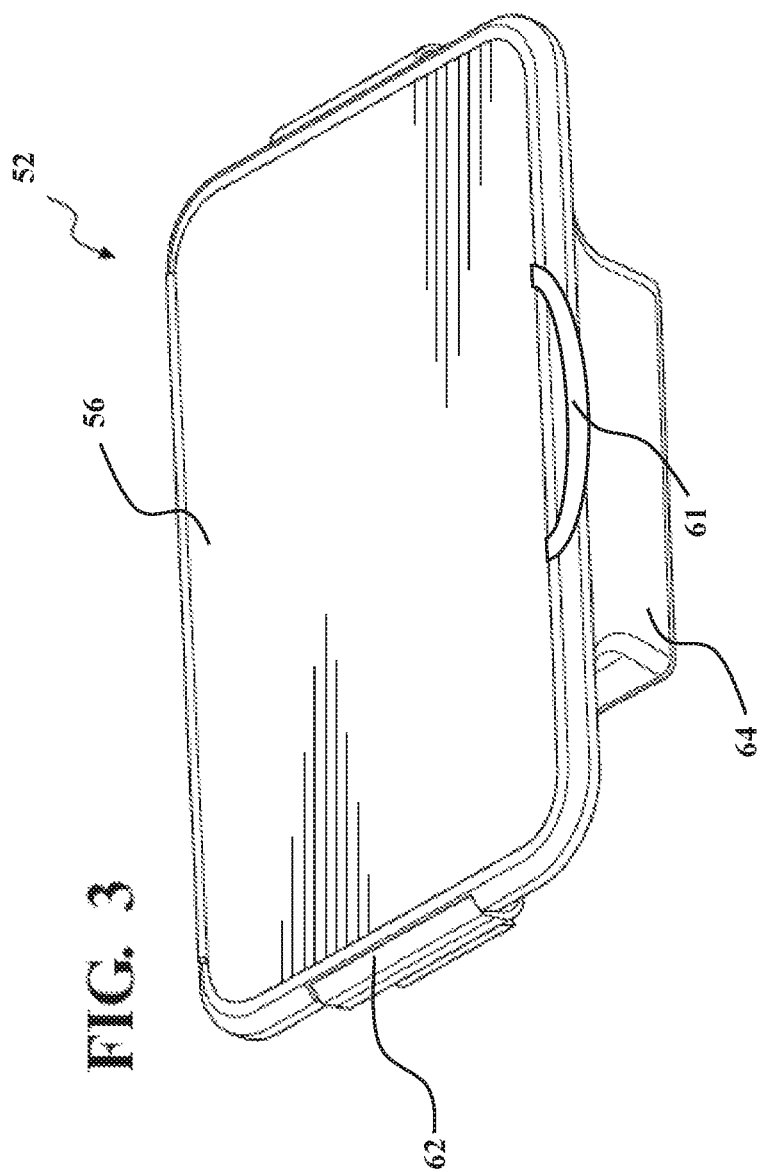
FIG. 3 is a front perspective view of the pediatric support module in the first configuration.
Figure 4:
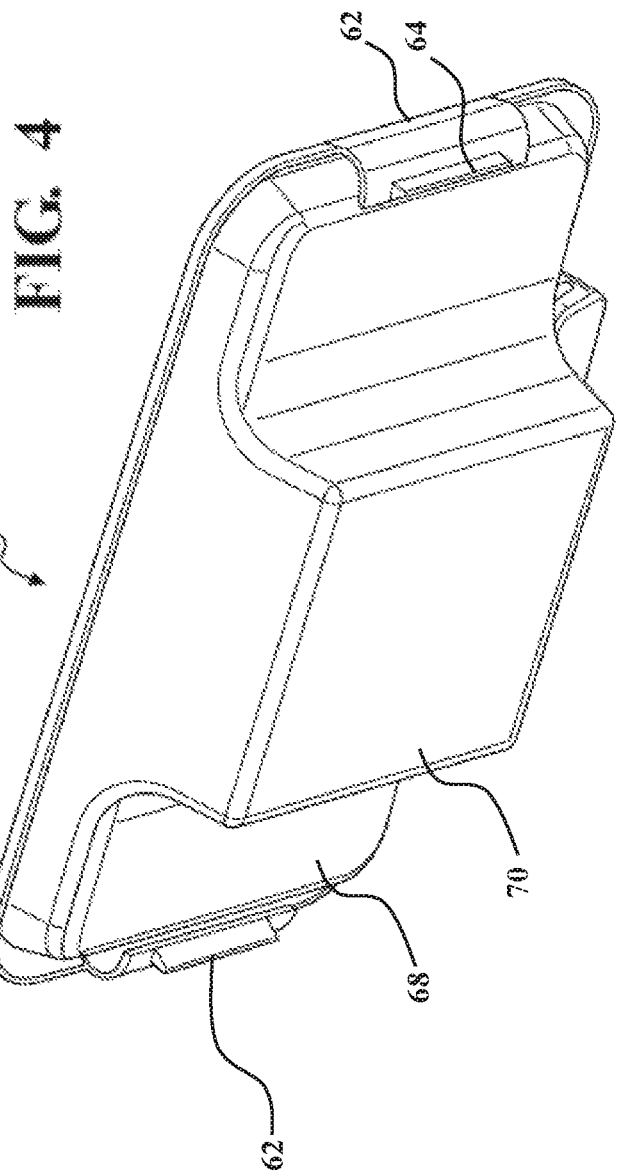
FIG. 4 is a rear perspective view of the pediatric support module in the first configuration.

Referring now to FIGS. 3 and 4, front and rear perspective views of the pediatric support module 52 in the first configuration are shown. The module lid 56 may be in an open position or a closed position. In FIGS. 3 and 4, the module lid 56 is shown in a closed position. The module lid 56 may comprise a handle 61 for lifting up the module lid 56 into an opened position. In some embodiments, the module lid 56 may comprise, instead of or in addition to the handle 61, one or more lid latch (not shown), such as a hinged latch integrated into the module lid 56. Utilizing an integrated lid latch or a similar latch design allows quick and easy locking/release of the module lid 56. The pediatric support module 52 may comprise latches 62 for securing the pediatric support module 52 to frame members 66 on the support frame 36 (not shown in FIGS. 3-4; see FIG. 9). The latches 62 comprise resilient tabs 64 that may be flexed by the user to engage/disengage the latches 62 with the frame members 66.

The pediatric support module 52 further comprises a hollow storage compartment 70 integrated into the module body 68, which is also hollow. The storage compartment 70 may be of any suitable size and/or shape, and may be used to store additional items or equipment. An additional cover, door, or opening may be present in the pediatric support module 52 to access the storage compartment 70, such as from the front of the pediatric support module 52 (see alternative hidden lines representing location of a door in FIG. 6).

Figure 5:
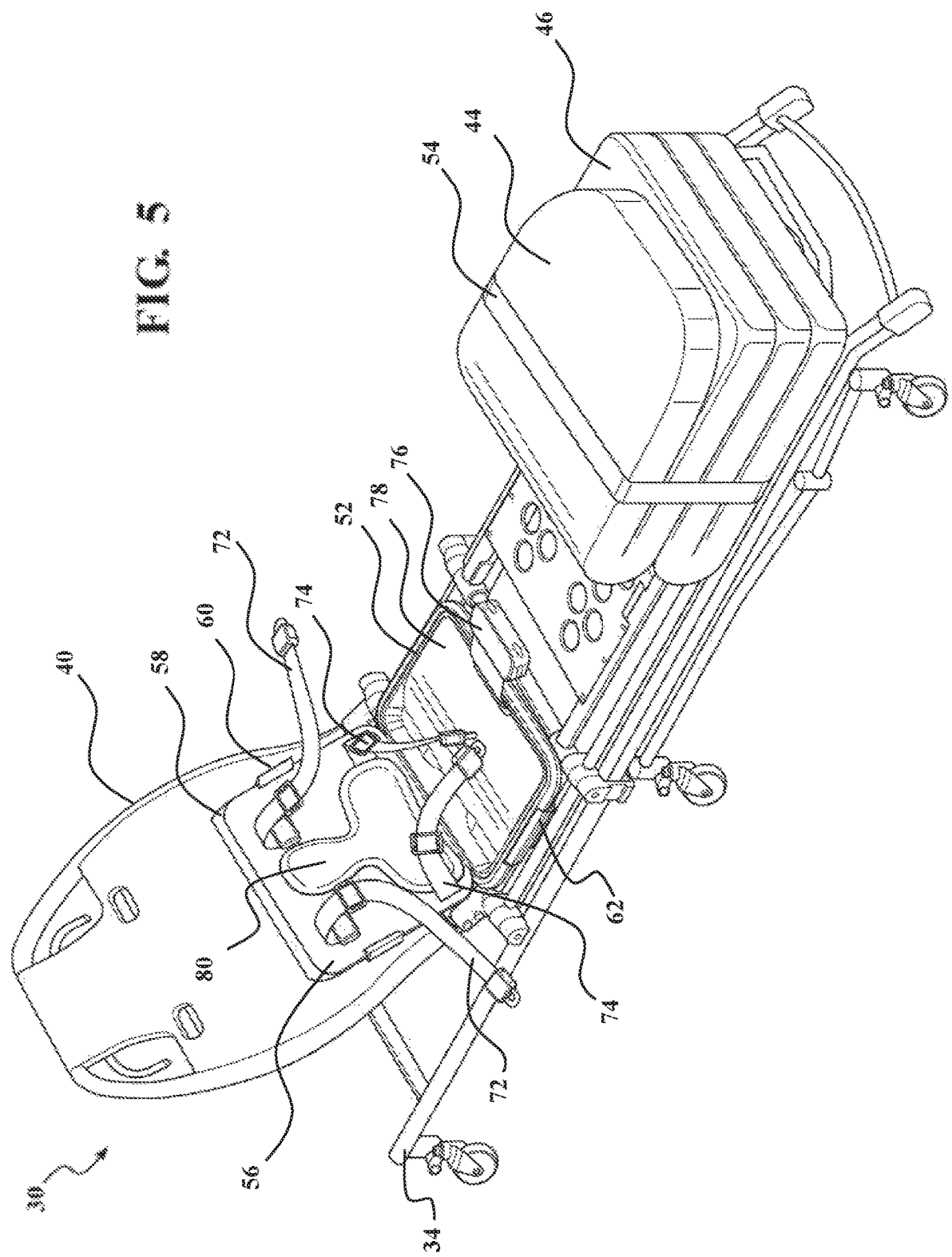
FIG. 5 is a perspective view of the patient support apparatus in a third apparatus configuration with the pediatric support module in a second module configuration.

Referring now to FIG. 5, the patient support apparatus 30 is shown in a third apparatus configuration with the pediatric support module 52 in a second module configuration. In the third apparatus configuration, the mattress 44 is still in the same position as in the second apparatus configuration, but the fowler section 40 of the patient support apparatus 30 is articulated relative to the base 34 into an elevated position. The fowler section 40 may be articulated and/or locked in any suitable position using any suitable elevating mechanism, such as that shown in U.S. Pat. No. 5,537,700, entitled, "Emergency Stretcher with X-Frame Support," filed on Apr. 19, 1994, hereby incorporated herein by reference. In the second module configuration, the module lid 56 is open and locked into place by the acceptor latches 60 of the lid connector 58 on the fowler section 40. The pediatric module 52 further comprises two sets of restraints: upper restraints 72 and lower restraints 74, all of which are coupled, and in some versions fixed, to the inside of module lid 56. Upper restraints 72 and lower restraints 74 may be fully adjustable to compensate for different sized patients. The restraints 72, 74 may comprise nylon or any other suitable material. Any or all of upper restraints 72 and lower restraints 74 may be fastened into a buckle housing 76, which is coupled to module body 68 to secure a child. Suitable restraints, restraint materials, and/or buckles for use therewith are shown in U.S. patent application Ser. No. 15/497,693, filed on Apr. 26, 2017, entitled, "Harness System for Patient Transport Apparatus," hereby incorporated herein by reference.

Inside the module body 68 may be a seat support 78, which may be comprised of any suitable material for supporting the patient while restrained in the pediatric support module 52, such as a solid material (e.g., plastic) or soft material (e.g., cushion, padding, etc.). The seat support 78 may be removable from the module body 68. The module lid 56 may further comprise a back support 80, which may be integrated or removable from the module lid 56, and may be comprised of any suitable material for supporting the patient while restrained in pediatric support module 52, such as a solid material (e.g., plastic) or soft material (e.g., cushion, padding, etc.).

Figure 6:
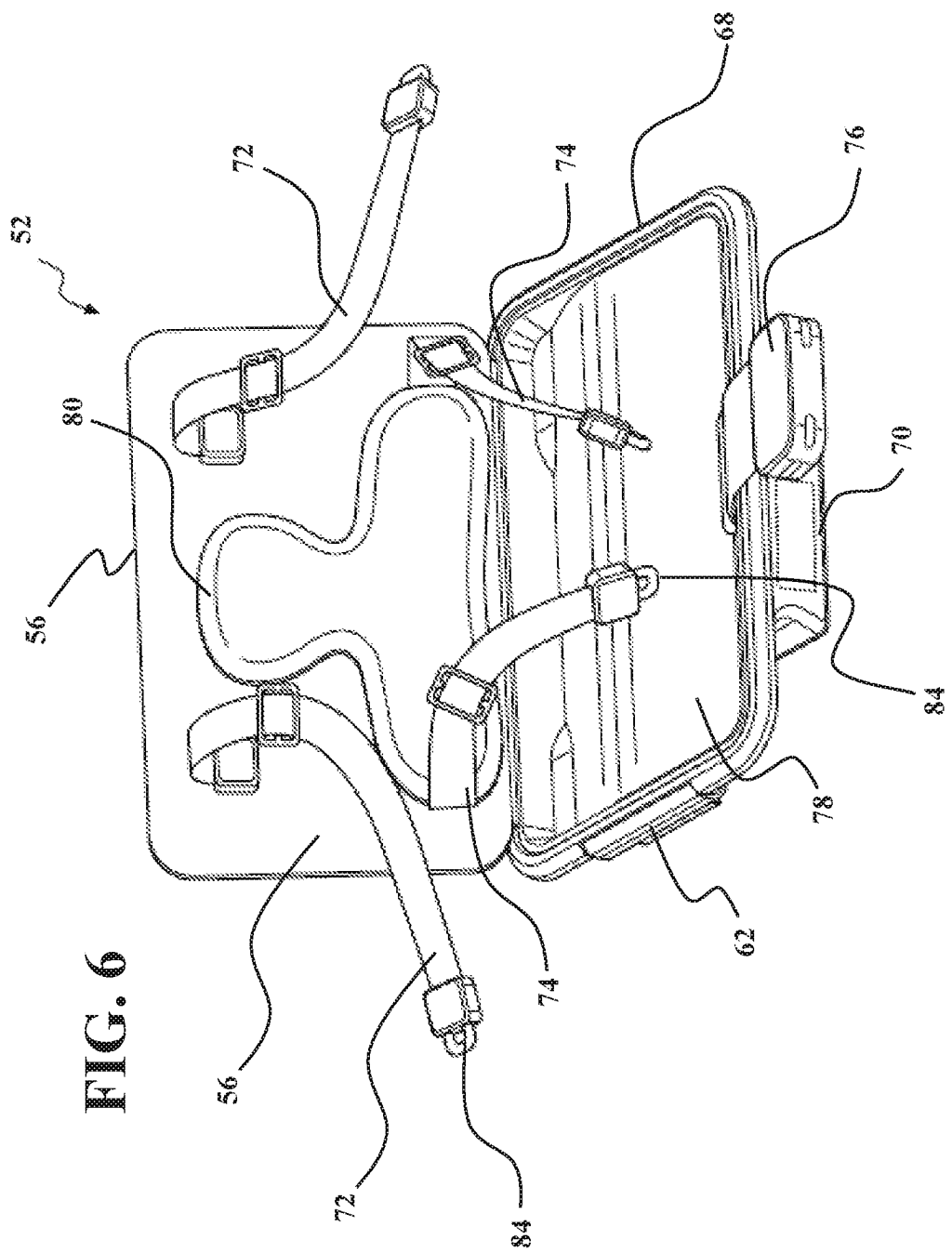
FIG. 6 is a front perspective view of the pediatric support module in the second configuration.
Figure 7:
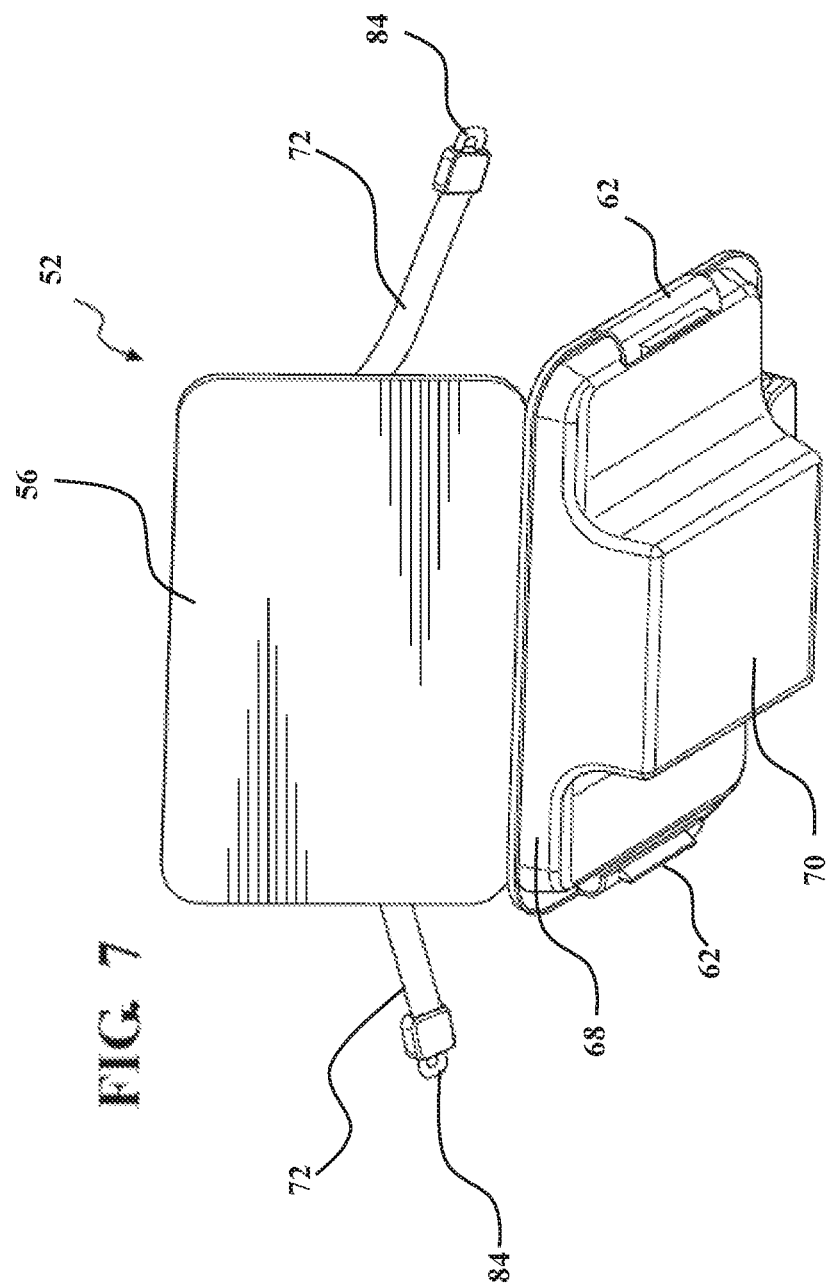
FIG. 7 is rear perspective view of the pediatric support module in the second configuration.

Referring now to FIGS. 6 and 7, front and rear perspective views of the pediatric support module in the second configuration are shown. Upper restraints 72 and lower restraints 74 each comprise a restraint tongue 84, discussed in more detail with reference to FIGS. 10-11.

Figure 8:
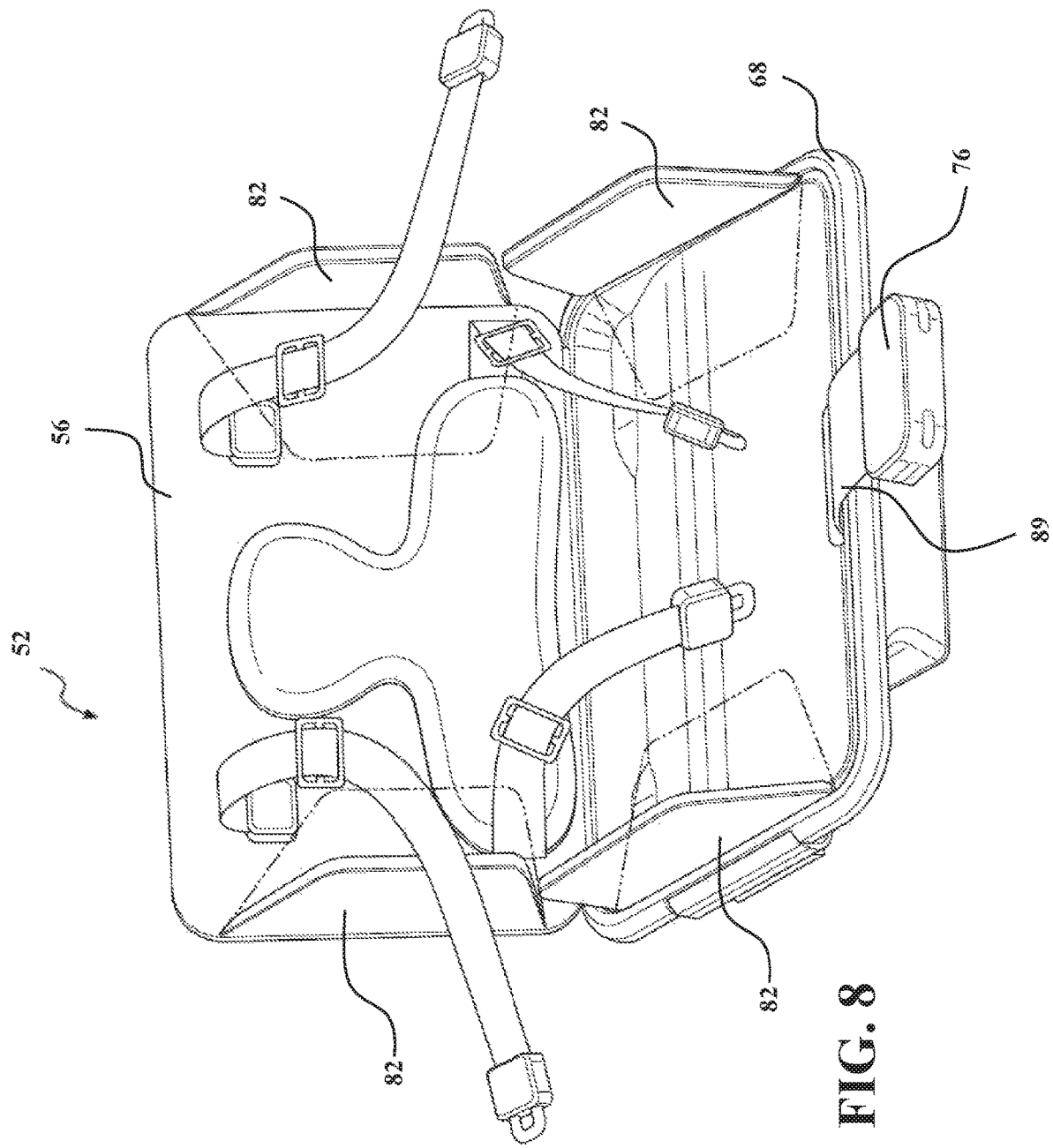
FIG. 8 is a front perspective view of the pediatric support module in the second configuration with side barriers.

Referring now to FIG. 8, a front perspective view of the pediatric support module 52 in the second configuration with side barriers 82. Side barriers 82 may be coupled to the patient support deck 38. The side barriers 82 may be hinged to the module lid 56 and/or the module body 68. When the module lid 56 is closed, the side barriers 82 may be folded inward to be stowed inside the module body 68 (shown in dotted lines). When the module lid 56 is open (as shown), the side barriers 82 may be flexed outward to provide additional security. For instance, it may be necessary to ensure the patient's arms and legs do not extend beyond the pediatric support module 52 for safety reasons (e.g., when the patient support apparatus 30 is being transported in tight spaces, such as an ambulance, where an appendage might be susceptible to being crushed or colliding with other objects that could cause injury). It will be appreciated that none, some, or all of the side barriers 82 may be utilized, as needed in a particular situation.

Figure 9:
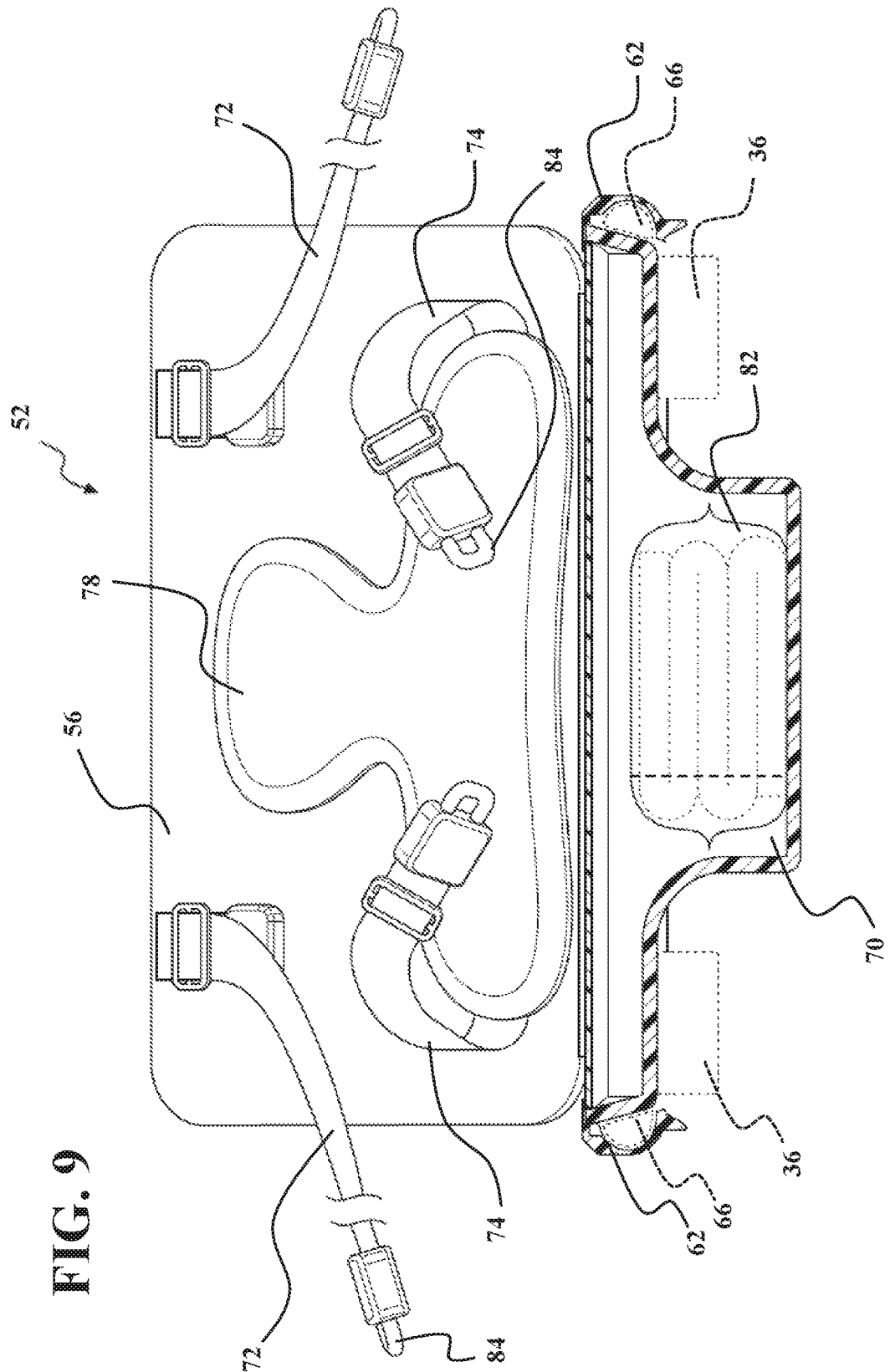
FIG. 9 is a front cross-sectional view of the pediatric support module in the second configuration.

Referring now to FIG. 9, a front cross-sectional view of the pediatric support module in the second configuration is shown. The inside of module body 68 and storage compartment 70 are shown. As previously discussed, the storage compartment 70 may hold any item or equipment that fits. In the illustrated embodiment, the storage compartment 70 holds a blanket within a sealed, tear-away package or pouch 82, which may be sterile. Although a blanket is shown in the illustrated embodiment, it will be understood that any item or combination of items (sheets, gloves, bandages/gauze/padding, medical instruments, pediatric-specific equipment, such as pediatric EKG pads, pediatric respirator masks, etc.) could be stored in the package 82 to prevent contamination of the item while not in use. The tear-away design allows for easy access to the item where time may be critical and/or where equipment such as a knife or scissors may not be available.

As discussed with reference to FIGS. 3 and 4, the latches 62 secure the pediatric support module 52 to frame members 66 on the support frame 36, to prevent the pediatric support module 52 from lifting out of the support frame 36 on its own. The latches 62 are shown in a locked position, with the tab 64 flexed toward a module body 68 such that the latch 62 engages the frame member 66, and the latch 62 is secured in place. To release the latch 62 into an unlocked position, the tab 64 may be flexed outwardly (away from the pediatric support module 52) to release the frame member 66, and thus disengage the pediatric support module 52 from the support frame 36. In other embodiments, other types of latches may be used, or the pediatric support module 52 may instead be permanently affixed to the support frame 36.

Figure 10:
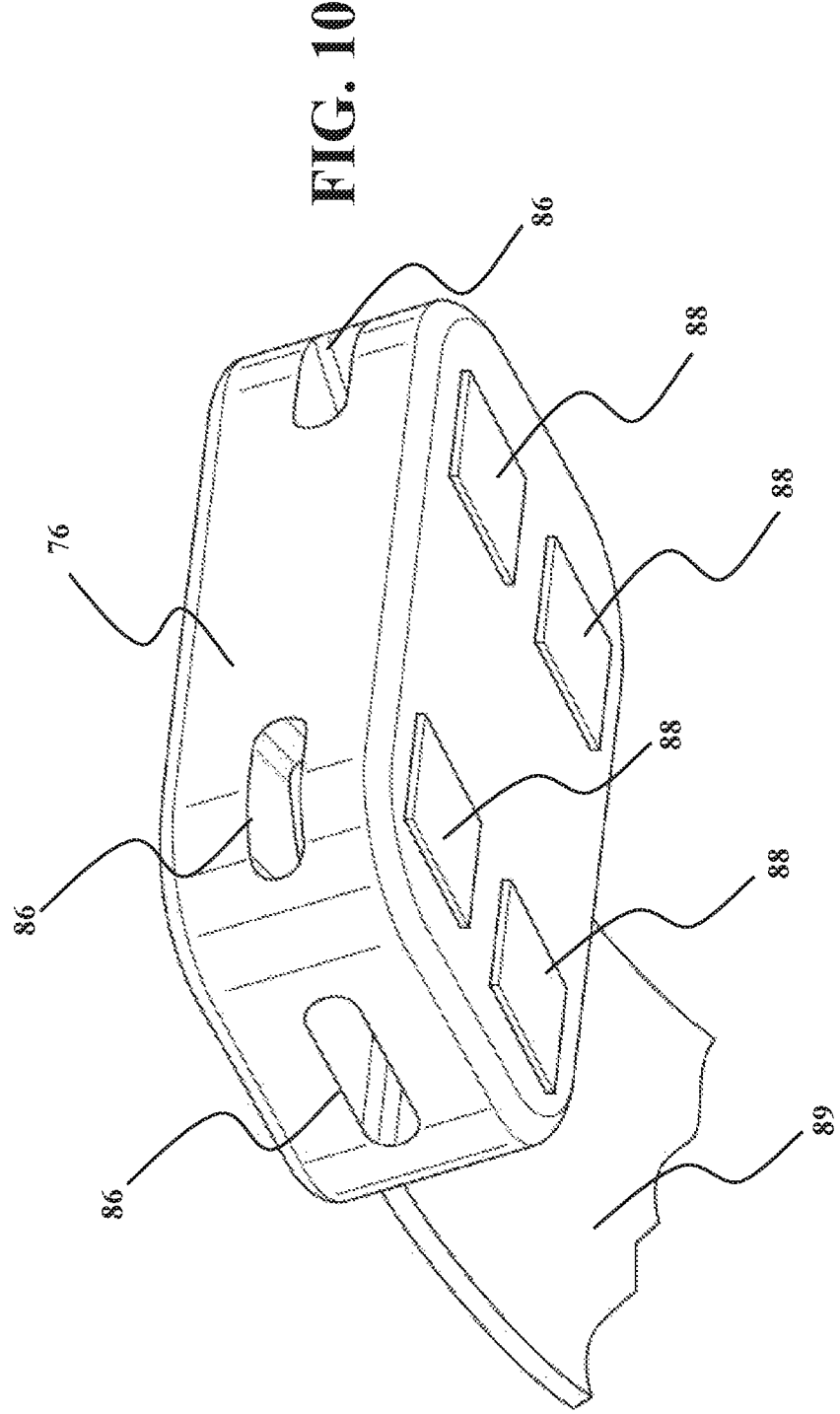
FIG. 10 is a perspective view of the buckle housing of the pediatric support module.

Referring now to FIG. 10, a perspective view of the buckle housing 76 of the pediatric support module 52 is shown. The buckle housing 76 is coupled to a buckle housing strap 89, which is fixed to the inside of module housing 68 (see FIGS. 6 and 8). The buckle housing 76 comprises apertures 86 for accepting the restraint tongues 84 of upper restraints 72 and lower restraints 74. The apertures 86 may be located on multiple sides of the buckle housing 76 for ease of access. For instance, in the illustrated embodiment, two apertures 86 are located on the top of the buckle housing 76, for accepting the restraint tongues 84 of upper restraints 72, and one aperture 86 is located on either side of the buckle housing 76, for accepting the restraint tongues 84 of lower restraints 74. It will be understood that different configurations of apertures 86 on the buckle housing 76 may be utilized. The buckle housing 76 further comprises release buttons 88, where one release button 88 corresponds to each aperture 86.

Figure 11:
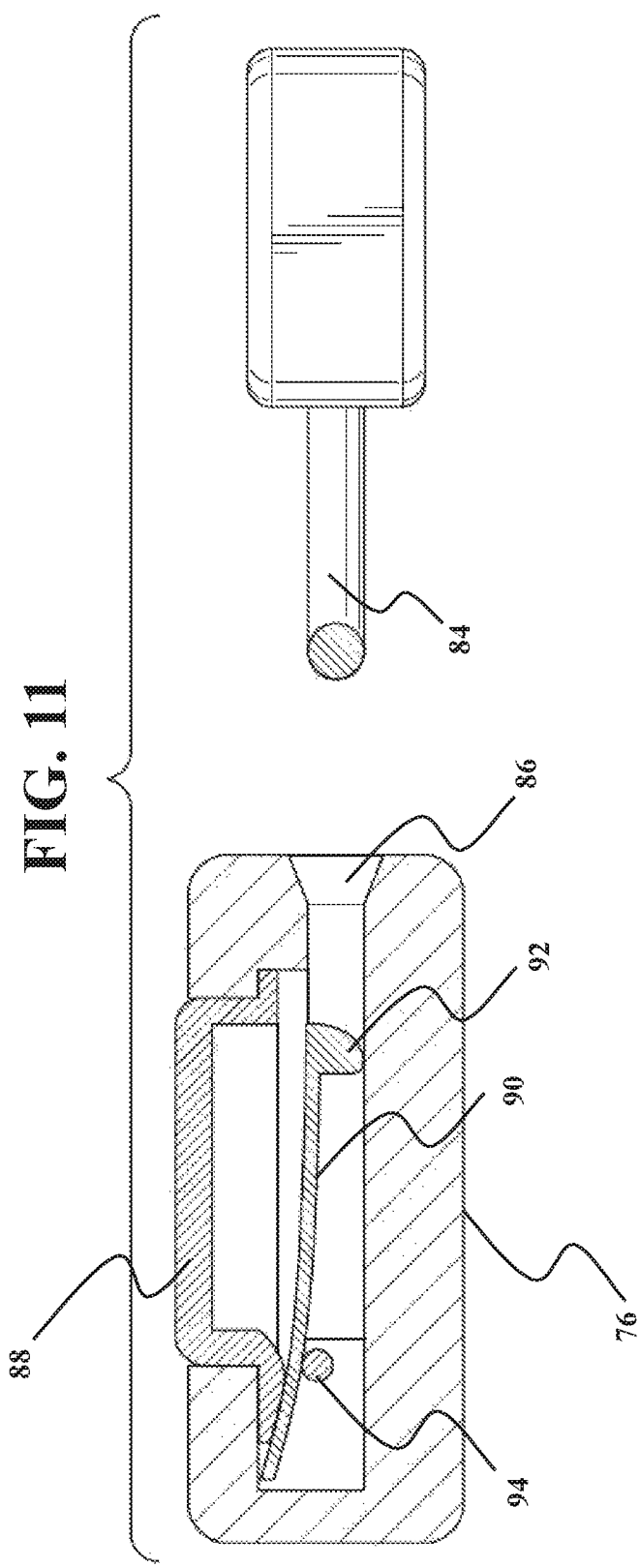
FIG. 11 is a side cross-sectional view of a restraint buckle tongue and a buckle housing of the pediatric support module.

Referring now to FIG. 11, a side cross-sectional view of the restraint tongue 84 and the buckle housing 76 of the pediatric support module 52 is shown. The restraint tongue 84 may be inserted into the aperture 86. Upon insertion, the restraint tongue 84 pushes against a resilient latch member 90. A first end of the latch member 90 comprises a locking projection 90 92 that is only slightly smaller than the aperture 86, and a second end of the latch member 90 is disposed above a pin 94. When the restraint tongue 84 engages against a curved front surface of the locking projection 92, the latch member 90 pivots on the pin 94 so that the locking projection 92 is lifted and the restraint tongue 84 can pass underneath the latch member 90. Once the restraint tongue 84 is underneath the latch member 90, the latch member 90 pivots back down on the pin 94 under its own spring-bias, and the locking projection 92 falls into the middle (empty space) of the restraint tongue 84. The locking projection 92 prevents the restraint tongue 84 from withdrawing from the aperture 86.

The release button 88 is disposed above the latch member 90. When the release button 88 is depressed, the release button 88 applies force to the second end of the latch member 90, which pivots on the pin 94 to lift the first end of the latch member 90. The locking projection 92 is lifted, allowing the restraint tongue 84 to be ejected from the aperture 86. This restraint buckling mechanism and its operation may be like that shown in U.S. Pat. No. 6,694,578, entitled, "Child Safety Belt Buckle Locking Mechanism," filed on May 15, 2003, hereby incorporated herein by reference.

Figure 12:
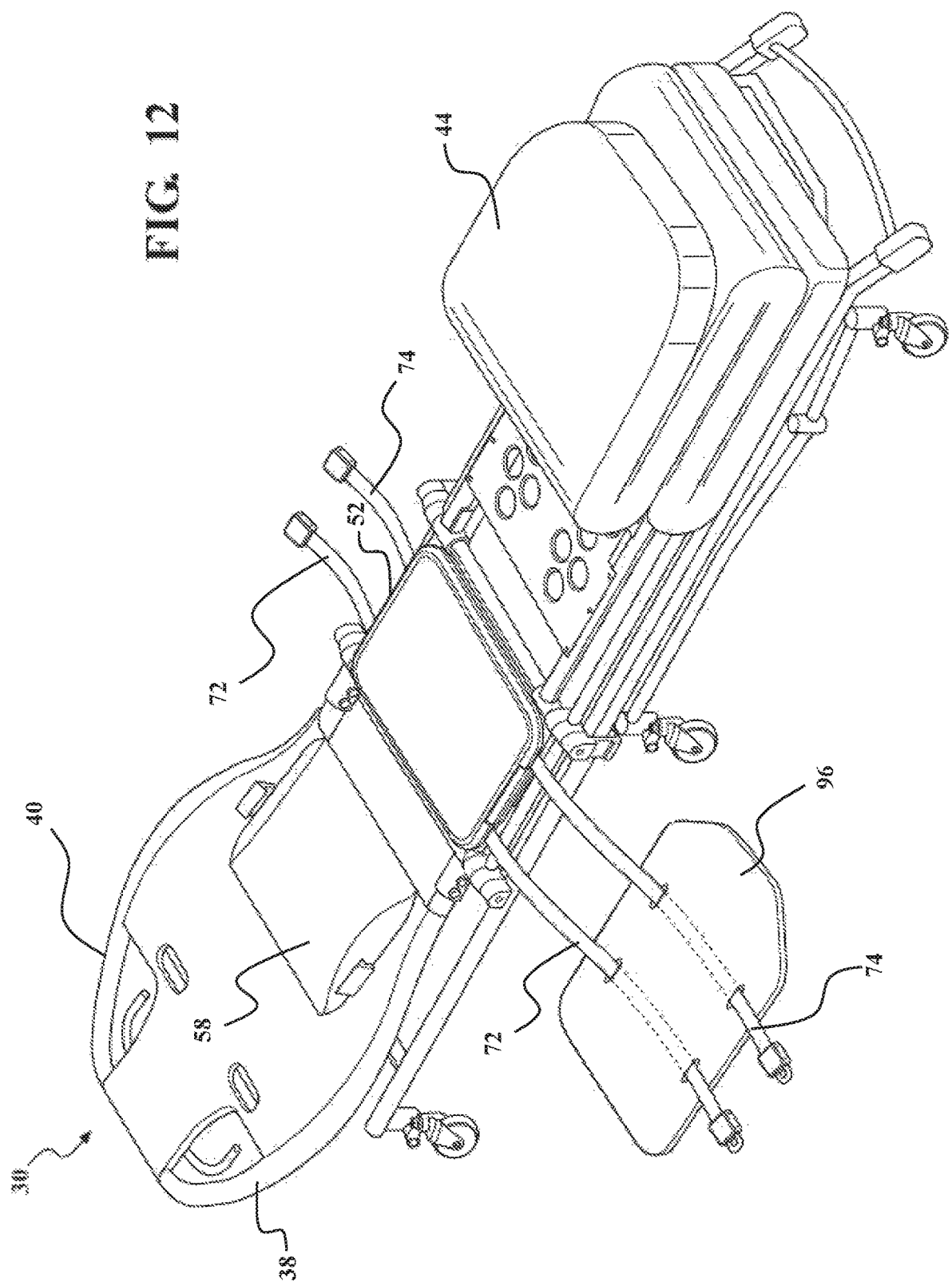
FIG. 12 is a perspective view of the patient support apparatus in a fourth apparatus configuration with the pediatric support module in a third module configuration.

Referring now to FIG. 12, a perspective view of the patient support apparatus in a fourth apparatus configuration with the pediatric support module in a third module configuration is shown. In the fourth apparatus configuration, the mattress 44 and the fowler section 40 are in the same position as in the second apparatus configuration. However, the mattress strap 54 is not used to restrain mattress 44. Moreover, the module lid 56 was opened and the upper and lower restraints 72, 74 were extended outside the pediatric module 52. The upper and lower restraints 72, 74 remain coupled, and in some versions fixed, to the inside of module lid 56. In this configuration, the module lid 56 has been closed again, leaving upper and lower restraints 72, 74 exposed outside of the pediatric module 52. A pediatric restraint panel 96 has been attached to one of the upper and lower restraints 72, 74. In some embodiments, the buckle housing 76 may be detachable from the upper and lower restraints 72, 74 to allow the pediatric restraint panel 96 to be coupled to the upper and lower restraints 72, 74.

Referring now to FIG. 13, a perspective view of the patient support apparatus in a fifth apparatus configuration with the pediatric support module in the third module configuration is shown. In the fifth apparatus configuration, the fowler section 40 is in the same position as in the second apparatus configuration, but the mattress 44 has been laid flat on top of the patient support deck 38, covering the pediatric support module 52, as in the first apparatus configuration. The upper and lower restraints 72, 74, and the pediatric restraint panel 96 attached thereto, remain exposed. The upper restraints 72 may be buckled to one another, and the lower restraints 74 may be buckled to one another, according to FIGS. 10-11, such that the pediatric restraint panel 96 covers a portion of the patient laying on the mattress 44, as shown. The additional pediatric restraint panel 96 secures the patient to the patient support apparatus 30 and prevents unsafe movement of the patient (e.g., while in transit).

Other restraint buckling mechanism designs are envisioned that may be utilized in place of the embodiment illustrated herein.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A patient support apparatus comprising:
a support structure comprising a head end, a foot end, a base, and a patient support deck, the patient support deck comprising a first fowler section at the head end and a foot section at the foot end, and a seat section between the first fowler section and the foot section, the first fowler section capable of articulating relative to the base; and
a pediatric support module integrated into the patient support deck at the seat section, the pediatric support module comprising a lid and a body, the body comprising a seat portion and a storage compartment disposed below the seat portion, wherein:
the lid is configured to articulate relative to the body and the first fowler section of the patient support deck,
the lid comprises a second fowler section of the pediatric support module, and
the second fowler section is configured to articulate relative to the body and relative to the first fowler section;
the patient support apparatus further comprising a mattress disposed above the patient support deck and configured to fold upon itself, and wherein a mattress strap retains the folded mattress at the foot end, in a position spaced from the pediatric support module in a direction towards the foot end.

2. The patient support apparatus of claim 1, wherein the lid of the pediatric support module comprises an adjustable restraint.

3. The patient support apparatus of claim 2, wherein the adjustable restraint comprises two adjustable upper restraints and two lower adjustable restraints.

4. The patient support apparatus of claim 1, wherein the lid is configured to couple to the first fowler section.

5. The patient support apparatus of claim 1, wherein the storage compartment is configured to store a pouch having a tear-away seal.

6. The patient support apparatus of claim 1, wherein the lid of the pediatric support module comprises a back section.

7. The patient support apparatus of claim 1, wherein the first fowler section further comprises a lid connector to connect the module lid to the first fowler section, the lid connector comprising a latch, wherein the lid connector is configured to accept the module lid and the latch is configured to secure the module lid on the first fowler section.

8. The patient support apparatus of claim 1, wherein the pediatric support module is removable from the patient support apparatus.

9. The patient support apparatus of claim 1, further comprising a side barrier coupled to one of the lid and the body.

10. The patient support apparatus of claim 1, wherein the mattress is configured to be removed from the support structure when the pediatric support module is in use.

* * * * *